(12) United States Patent
Tang et al.

(10) Patent No.: US 11,877,974 B2
(45) Date of Patent: Jan. 23, 2024

(54) MASSAGE GUN WITH IMPROVED CONNECTING CABLE

(71) Applicant: ZheJiang E-cozy Electronic Technology Co., Ltd., Zhejiang Province (CN)

(72) Inventors: Shousheng Tang, Wenzhou (CN); Daojin Tang, Zhejiang (CN)

(73) Assignee: ZHEJIANG E-COZY ELECTRONIC TECHNOLOGY CO., LTD., Wenzhou (CN)

( * ) Notice: Subject to any disclaimer, the term of this patent is extended or adjusted under 35 U.S.C. 154(b) by 424 days.

(21) Appl. No.: 17/316,025

(22) Filed: May 10, 2021

(65) Prior Publication Data

US 2022/0168175 A1 Jun. 2, 2022

(30) Foreign Application Priority Data

Nov. 27, 2020 (CN) .......................... 202011364393.6
Nov. 27, 2020 (CN) .......................... 202022814150.X

(51) Int. Cl.
*A61H 23/00* (2006.01)
*H01B 7/22* (2006.01)

(52) U.S. Cl.
CPC ............. *A61H 23/006* (2013.01); *H01B 7/22* (2013.01); *A61H 2201/0153* (2013.01);
(Continued)

(58) Field of Classification Search
CPC .......... A61H 23/006; A61H 2201/0153; A61H 2201/0207; A61H 2201/0214; A61H 2201/10; A61H 2201/025; A61H 2201/14; A61H 23/02; A61H 39/00; A61H 2201/0157; A61H 2201/0165; A61H 2201/1664; A61H 2201/50; A61H 2201/1657; A61H 23/0218; A61H 2201/1207; A61H 2201/1678;
(Continued)

(56) References Cited

U.S. PATENT DOCUMENTS 2,782,491 A * 2/1957 Cole ...................... H01R 4/023
29/879
5,925,002 A * 7/1999 Wollman ........... A61H 23/0263
601/80
(Continued)

*Primary Examiner* — Kendra D Carter
*Assistant Examiner* — Jaeick Jang
(74) *Attorney, Agent, or Firm* — Chun-Ming Shih; LANWAY IPR SERVICES

(57) ABSTRACT

A massage gun includes a gun body, a massage head arranged on the gun body, an auxiliary physiotherapy assembly arranged in the massage head, a main circuit board arranged in the gun body, and a connecting cable electrically connected to the auxiliary physiotherapy assembly and the main circuit board, where the connecting cable is made of a conductive wire resistant to high-speed bending. The connecting cable electrically connected to the auxiliary physiotherapy assembly in the massage head is made of the conductive wire resistant to high-speed bending, which solves the problem that the connecting cable breaks easily when the massage gun performs high-speed piston movement. Because the connecting cable does not break easily, electrical connection can be maintained, thereby prolonging the service life of the massage gun, and reducing use costs.

5 Claims, 5 Drawing Sheets

(52) U.S. Cl.
CPC ............... *A61H 2201/0207* (2013.01); *A61H 2201/0214* (2013.01); *A61H 2201/10* (2013.01)

(58) Field of Classification Search
CPC .... A61H 2201/1685; A61H 2201/0107; A61H 2201/5082; A61H 2201/5058; A61H 23/0045; A61H 2205/02; A61H 2205/04; A61H 2205/06; A61H 2205/062; A61H 39/007; A61H 7/00; A61H 1/00; A61H 1/008; A61H 23/008; A61H 2023/0209; A61H 2023/0227; A61H 23/0236; A61H 23/0245; A61H 23/0254; A61H 23/0263; A61H 2023/0272; A61H 2023/0281; A61H 2023/029; H01B 7/22; H01B 7/00; H01B 7/18; A61F 2007/0078; A61F 2007/007; A61F 2007/0087; A61F 2007/0095; A61F 7/00; A61F 7/007; A61N 1/26; A61N 1/322; A61N 1/18

See application file for complete search history.

(56) References Cited

U.S. PATENT DOCUMENTS

| | | | |
|---|---|---|---|
| 6,818,839 B2* | 11/2004 | Hosaka | H01R 12/57 174/262 |
| 2011/0147079 A1* | 6/2011 | Dlugas | H01B 7/0009 174/110 SR |
| 2020/0268594 A1* | 8/2020 | Pepe | A61H 15/0085 |

* cited by examiner

MASSAGE GUN WITH IMPROVED CONNECTING CABLE

This application claims priorities to Chinese Patent Application No. 202022814150.X, filed 27 Nov. 2020 and Chinese Patent Application No. 202011364393.6, filed 27 Nov. 2020, the contents of which are hereby incorporated by reference in their entirety.

TECHNICAL FIELD

The present disclosure relates to the technical field of massage devices, and in particular, to a novel massage gun which has a long service life, causes a wire not to be broken easily and has cooling and heating functions.

BACKGROUND

A massage gun is a massage device, having a structure like a pistol. The massage gun includes a transverse housing and a longitudinal handle, and a massage head is arranged at a front end of the housing. The massage head can vibrate back and forth. The massage head is pressed against the muscles to vibrate the muscles to achieve the effect of relaxing the muscles and promoting blood circulation. In order to better meet people's needs for multiple functions, the existing massage gun further needs to have other auxiliary physiotherapy functions in addition to the vibration function, such as cooling and heating and electric shock. A corresponding auxiliary physiotherapy assembly needs to be arranged in the massage head, and a wire and a signal line are led from a main circuit board in the handle into the massage head at a front end of the housing, so as to provide power and control signals.

The applicant found that the prior art has at least the following technical problems:

Wire materials and structures used in the massage guns currently on the market cannot solve the problem of metal fatigue when the massage gun performs high-speed piston movement. For example, copper wires or other conventional conductive wires break easily after they quickly swing or shake for a long time.

SUMMARY

An object of the present disclosure is to provide a novel massage gun, so as to solve the technical problem that in the prior art, a wire breaks easily when the massage gun moves at a high speed.

To achieve the foregoing objective, the present disclosure provides the following technical solutions:

A novel massage gun provided according to the present disclosure, including a gun body, a massage head arranged on the gun body, an auxiliary physiotherapy assembly arranged in the massage head, a main circuit board arranged in the gun body, and a connecting cable electrically connected to the auxiliary physiotherapy assembly and the main circuit board, wherein the connecting cable is made of a conductive wire resistant to high-speed bending.

As a further improvement of the present disclosure, the conductive wire resistant to high-speed bending comprises an outer skin and an inner core, the outer skin is made of an insulating material, and the inner core is made of ultrafine metal fiber filaments.

As a further improvement of the present disclosure, the ultrafine metal fiber filament is a stainless steel fiber filament or a silver fiber filament.

As a further improvement of the present disclosure, an auxiliary connecting part is further arranged between the connecting cable and the auxiliary physiotherapy assembly, and the auxiliary connecting part is made of a weldable conductive material.

As a further improvement of the present disclosure, one end of the auxiliary connecting part is riveted to the connecting cable, and the other end thereof is welded to the auxiliary physiotherapy assembly.

As a further improvement of the present disclosure, the auxiliary connecting part is made of a copper material.

As a further improvement of the present disclosure, the gun body comprises a handle and a housing vertically connected to the handle, and a wire bridge structure for the connecting cable to pass through is provided on a side wall of the handle corresponding to the housing.

As a further improvement of the present disclosure, the auxiliary physiotherapy assembly comprises a physiotherapy module, a physiotherapy control circuit board, and an aviation plug male connector that are electrically connected in sequence, an aviation plug female connector detachably and electrically connected to the aviation plug male connector is arranged in the housing, and the auxiliary connecting part is welded to the aviation plug female connector.

As a further improvement of the present disclosure, a piston part, a guide groove part, a guide groove silicon gel part, a seal cover, and a positioning part are arranged in the housing, the guide groove part is in contact connection with an inner wall of the housing through the guide groove silicon gel part, the piston part is slidably arranged in the guide groove part, the aviation plug female connector passes through the seal cover and is then screwed to the positioning part, the positioning part is fixedly connected to a partition plate in an inner cavity of the piston part, and the partition plate is provided with a first opening for the connecting cable to pass through; the positioning part has a hollow structure with a cavity for accommodating the aviation plug female connector, and the connecting cable passes through the first opening and then enters the inner cavity of the positioning part to be riveted to the auxiliary connecting part.

As a further improvement of the present disclosure, the positioning part is made of a plastic material and comprises a clamping portion and a connecting portion, and the connecting portion has a hollow cylindrical structure with an inner wall provided with a threaded section; the clamping portion has a boss structure formed by extending outward and vertically from one end of the connecting portion, the specification and shape of the clamping portion are adapted to the shape and specification of the inner cavity of the piston part, the clamping portion is provided with a positioning hole, and a threaded hole is formed in a corresponding position of the partition plate.

Compared with the prior art, the present disclosure has the following beneficial effects:

The novel massage gun provided by the present disclosure is a multifunctional massage gun, which not only has a percussion function, but also has auxiliary physiotherapy functions such as cooling and heating or electric shock; the connecting cable electrically connected to the auxiliary physiotherapy assembly in the massage head is made of a conductive wire resistant to high-speed bending, which solves the problem that the connecting cable breaks easily when the massage gun performs high-speed piston movement; because the connecting cable does not break easily, electrical connection can be maintained, which prolongs the service life of the massage gun, and reduces use costs; the auxiliary connecting part is used, and with the aid of processes such as riveting, the connecting cable can be welded to the aviation plug female connector, thereby solving the problem that the connecting cable cannot be welded when made of ultrafine stainless steel fiber filaments; the aviation plug has a plurality of holes for distinguishing between positive and negative poles and signal transmission; in order to ensure the correctness of the plug sequence, a plastic positioning part with a specific positioning function is adopted, and the aviation plug is fixed on the positioning part through threads, and then the positioning part is connected to a partition plate in an inner cavity of a piston part through two positioning holes, and is fixed at a rear end by using a screw; the wire bridge structure is provided, the stainless steel fiber filament is wound on the wire bridge structure, and then two ends thereof extend into the handle and the housing respectively; and the winding at the wire bridge structure is flexibly wound, which avoids a dead point of a rigid connection wire and acts as a fulcrum.

BRIEF DESCRIPTION OF THE DRAWINGS

In order to explain the embodiments of the present disclosure or the technical solutions in the prior art more clearly, the following will briefly describe the accompanying drawings that need to be used in the description of the embodiments or the prior art. Obviously, the accompanying drawings in the following description show only some embodiments of the present disclosure, and those of ordinary skill in the art can still derive other accompanying drawings from these accompanying drawings without creative efforts.

Reference signs in drawings: 1. gun body; 11. handle; 12. housing; 121. aviation plug female connector; 122. piston part; 123. guide groove part; 124. guide groove silicon gel part; 125. seal cover; 126. positioning part; 127. partition plate; 2. massage head; 21. massage head cover; 22. massage head body; 23. anti-collision part; 3. main circuit board; 4. connecting cable; 5. auxiliary connecting part; 6. wire bridge structure; 7. physiotherapy module 8. physiotherapy control circuit board; 9. aviation plug male connector; 100. power supply assembly; 110. reciprocating driving mechanism; 1101. crank; 1102. connecting rod.

DESCRIPTION OF THE EMBODIMENTS

To make the object, technical solution and advantages of the present disclosure clearer, the following describes the technical solutions of the present disclosure in detail. Apparently, the described embodiments are merely some rather than all of the embodiments of the present disclosure. All other implementations obtained by a person of ordinary skill in the art based on the embodiments of the present disclosure without creative efforts shall fall within the protection scope of the present disclosure.

Figure 1:
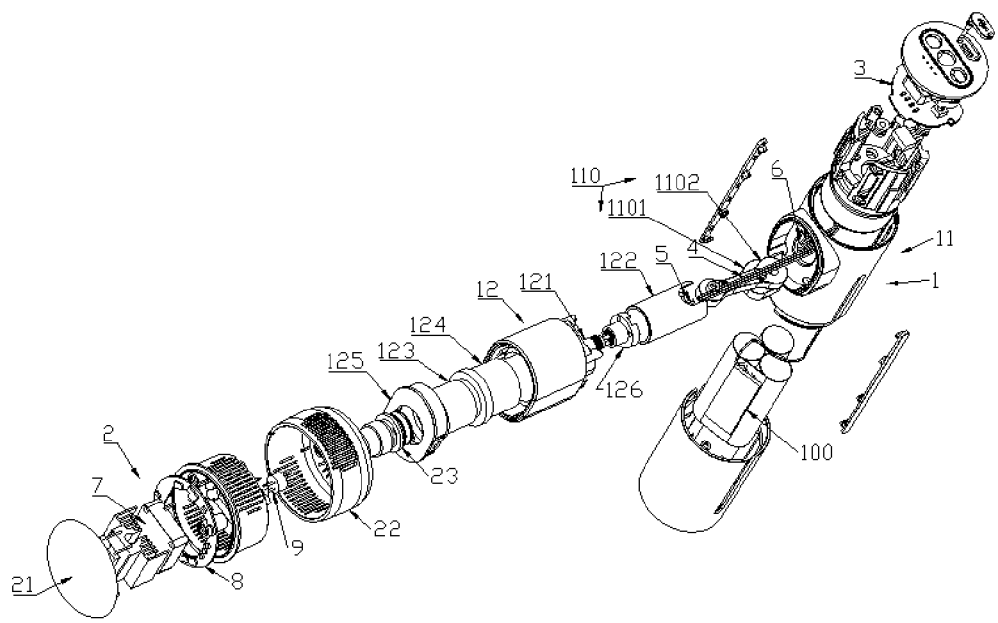
FIG. 1 is an exploded view of a massage gun according to the present disclosure from a perspective.
Figure 4:
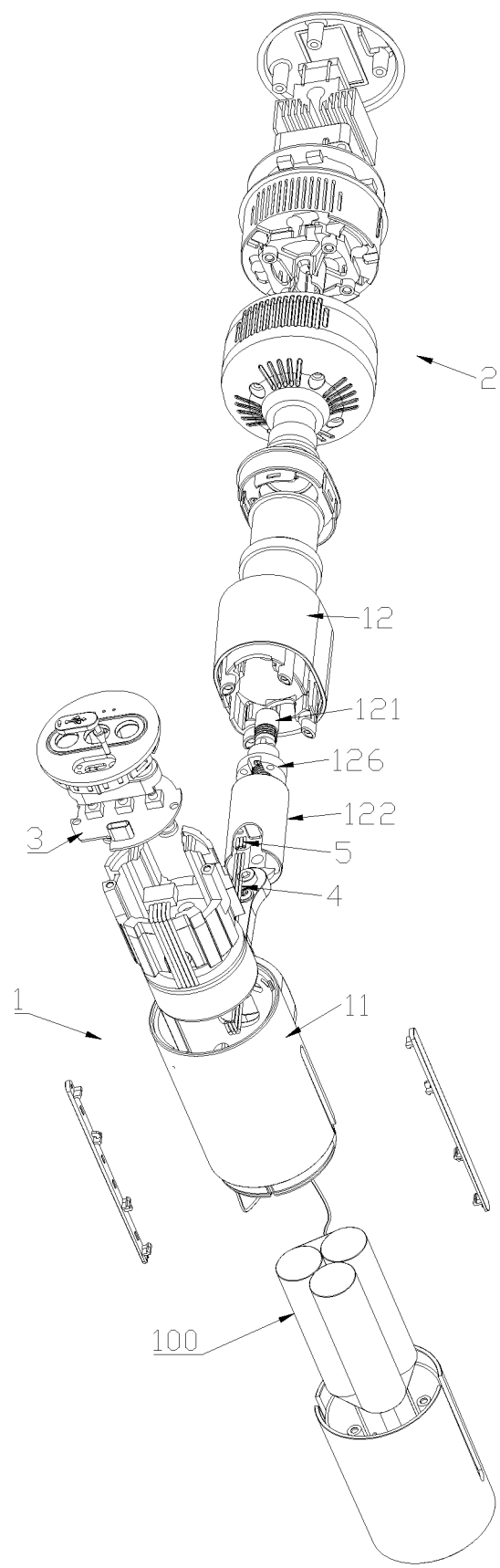
FIG. 4 is an exploded view of the massage gun of the present disclosure from another perspective.

As shown in FIG. 1 and FIG. 4, the present disclosure provides a novel massage gun, including a gun body 1, a massage head 2 arranged on the gun body 1, an auxiliary physiotherapy assembly arranged in the massage head 2, a main circuit board 3 arranged in the gun body 1, and a connecting cable 4 electrically connected to the auxiliary physiotherapy assembly and the main circuit board 3, where the connecting cable 4 is made of a conductive wire resistant to high-speed bending.

Further, the auxiliary physiotherapy assembly may be a cooling and heating assembly or an electric shock assembly, or the like. The connecting cable 4 includes a power supply cable and a signal cable.

The novel massage gun provided according to the present disclosure is a multifunctional massage gun, which not only has a percussion function, but also has auxiliary physiotherapy functions such as cooling and heating or electric shock; the connecting cable electrically connected to the auxiliary physiotherapy assembly in the massage head is made of a conductive wire resistant to high-speed bending, which solves the problem that the connecting cable breaks easily when the massage gun performs high-speed piston movement; because the connecting cable does not break easily, electrical connection can be maintained, which prolongs the service life of the massage gun, and reduces use costs.

In an optional implementation of the present disclosure, the conductive wire resistant to high-speed bending comprises an outer skin and an inner core, the outer skin is made of an insulating material, and the inner core is made of ultrafine metal fiber filaments.

Further, the insulating material may be a TPEE material.

It should be noted that, in an optional implementation of the present disclosure, the ultrafine metal fiber filament is a stainless steel fiber filament or a silver fiber filament.

It should be noted that there are 6000 fiber filaments in the connecting cable made of the stainless steel fiber filaments having a diameter of 0.96 mm.

A stainless steel fiber is a novel industrial material developed in recent years and pertains to an important field of modern science. The stainless steel fiber is generally made by using special processes such as composite assembly, multiple bundling drawing, annealing, and solution treatment and taking French Yinfei 316L stainless steel, and each strand has thousands or tens of thousands of fiber filaments. The surface area of the stainless steel fiber is very large, so that the stainless steel fiber has extraordinary performance in terms of internal structure, magnetism, thermal resistance, melting point, etc. The stainless steel fiber filament may have a diameter of 1-2 microns, an elongation greater than 1%, and a fiber strength of 1200-1800 Mpa, which even exceeds the tensile strength of the material itself. Because the internal structure, physical and chemical properties, surface properties, etc. of the stainless steel fiber have significant changes during the fiberization process, the stainless steel fiber not only has the advantages of high elasticity modulus, high bending strength and tensile strength, etc. inherent in metal materials, but also has some special properties and a wide range of uses of non-stainless steel fibers. Compared with organic and inorganic fibers, the stainless steel fiber has higher elasticity, flexibility (the softness of the stainless steel fiber with a diameter of 8 μm is equivalent to that of a hemp fiber with a diameter of 13 μm), flexibility, adhesiveness (when appropriate surface treatment is performed, the fiber has good performance of jointing to other materials, which is suitable for any kind of composite material), wear resistance, high temperature resistance (in an oxidizing environment, the material can be used continuously at 600° C.), corrosion resistance (resistance to HNO3, alkali and organic solvent corrosion), better ventilation, electrical conductivity, magnetic permeability, thermal conductivity, self-lubricating and sintering properties. In addition, the unique environmental friendliness and reusability of the stainless steel fiber greatly increase its use value in social production and life. Composites composed of the stainless steel fiber as the base material have been widely developed and utilized in the electronics, chemical, machinery, military, textile, food, medicine and other industries, opening up broad application prospects.

Figure 2:
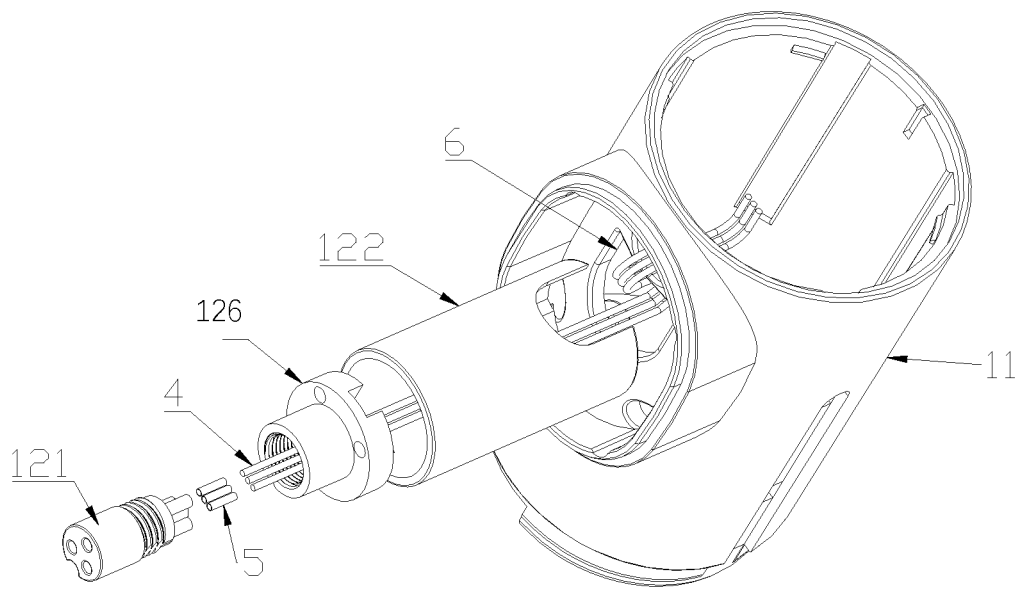
FIG. 2 is a first exploded view of a partial structure of the massage gun according to the present disclosure.
Figure 5:
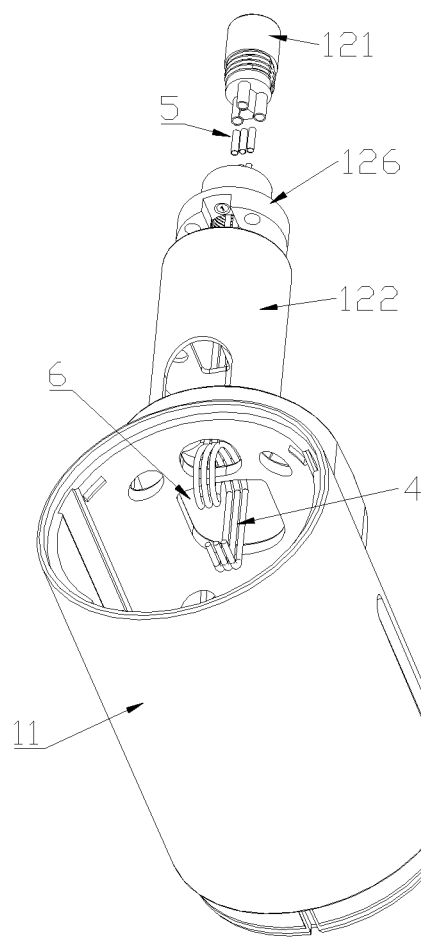
FIG. 5 is a second exploded view of a partial structure of the massage gun according to the present disclosure.

As shown in FIG. 2 and FIG. 5, further, an auxiliary connecting part 5 is further arranged between the connecting cable 4 and the auxiliary physiotherapy assembly; and the auxiliary connecting part 5 is made of a weldable conductive material.

Because the connecting cable 4 is made of ultrafine stainless steel fiber filaments and the ultrafine stainless steel fiber wire cannot be welded, in order to implement connection, the auxiliary connecting part 5 is used, one end of the auxiliary connecting part 5 is riveted to the connecting cable 4, and the other end thereof is welded to the auxiliary physiotherapy assembly.

The auxiliary connecting part is used, and with the aid of processes such as riveting, the connecting cable can be welded to the aviation plug female connector, thereby solving the problem that the connecting cable cannot be welded when made of ultrafine stainless steel fiber filaments.

Further, the auxiliary connecting part 5 is made of a copper material, or certainly, may be made of other conductive materials such as aluminum and iron, which is not limited to the auxiliary connecting part 5 made of copper.

As shown in FIG. 2 and FIG. 5, in an optional implementation of the present disclosure, the gun body 1 includes a handle 11 and a housing 12 vertically connected to the top of the handle 11. A wire bridge structure 6 for the connecting cable 4 to pass through is arranged on a side wall of the handle 11 corresponding to the housing 12.

The stainless steel fiber filament is wound on the wire bridge structure 6, and then two ends thereof extend into the handle 11 and the housing 12 respectively; and the winding at the wire bridge structure 6 is flexibly wound, which avoids a dead point of a rigid connection wire and acts as a fulcrum.

Further, the wire bridge structure 6 is provided with an upper threading hole and a lower threading hole formed in the side wall of the handle 11, and a fixed support beam is formed between the two threading holes. The connecting cable 4 passes through one threading hole and then penetrates the other threading hole around the fixed support beam, and then passes through the first threading hole to implement winding, fixation and supporting of the connecting cable 4. When the connecting cable 4 at this position is wound, a flexible winding method may be adopted, that is, the contact area between the connecting cable 4 and the fixed support beam is as small as possible. In order to ensure the flexible winding at the position as much as possible, the specifications of the two threading holes are greater than the diameter of the connecting cable 4, and the specification of one of the threading holes is much greater than the diameter of the connecting cable 4 to leave an enough space for cable routing.

In an optional implementation of the present disclosure, the auxiliary physiotherapy assembly includes a physiotherapy module 7, a physiotherapy control circuit board 8, and an aviation plug male connector 9 which are sequentially electrically connected, an aviation plug female connector 121 detachably and electrically connected to the aviation plug male connector 9 is arranged in the housing 12, and the auxiliary connecting part 5 is welded to the aviation plug female connector 121.

Further, it should be further noted that the handle 11 and the housing 12 have an L-shaped structure, forming a massage gun similar to a "gun"; the massage head 2 is located at a front end of the housing 12, and a power supply assembly 100, a reciprocating driving mechanism 110 and a main circuit board 3 are arranged in the handle 11; the power supply assembly 100 is electrically connected to the main circuit board 3 through an ordinary wire, the main circuit board 3 is electrically connected to the reciprocating driving mechanism 110 through an ordinary wire, and the reciprocating driving mechanism 110 is in transmission connection with the massage head 2, thereby driving the massage head 2 to reciprocate in an axial direction to form a continuous percussion action.

In the present disclosure, the power supply assembly 100 includes a rechargeable battery module.

The following takes the physiotherapy module 7 being a cooling and heating assembly as an example for specific description:

The cooling and heating assembly is arranged in the massage head 2, so that the massage head 2 can absorb heat or cold to heat up or cool down, so as to apply the massage head to the surface of the human body receiving massage physiotherapy for thermal therapy or cold compress.

As shown in FIG. 1 and FIG. 4, the massage head 2 includes a massage head cover 21, a massage head body 22, and an anti-collision part 23; and the massage head body 22 is detachably arranged on the massage head cover 21. Specifically, the massage head body 22 may be connected to the massage head cover 21 in a mode of snap connection or plug connection, and an accommodating cavity for accommodating the cooling and heating assembly is formed between the two. The aviation plug male connector 9 is fixed on the massage head cover 21 and electrically connected to the cooling and heating assembly. The massage head 2 is made of a metal material.

Further, the massage head cover 21 is in the shape of a bell mouth and includes an expansion part and a base part. An outer side of the base part is sleeved with the anti-collision part 23; and when the massage head 2 is in transmission connection with the reciprocating driving mechanism 110, the base part penetrates into the housing 12 and is in contact with an inner wall of the housing 12 through the anti-collision part 23.

It should be noted that the anti-collision part 23 has a cylindrical structure and is made of silica gel.

As shown in FIG. 1, further, the cooling and heating assembly includes a heat dissipation aluminum part, a cooling and heating sheet, a cooling fan, and a temperature sensing element. The temperature sensing element is fixed in the massage head body 22 and electrically connected to the physiotherapy control circuit board 8. The heat dissipation aluminum part has a U-shaped structure with the top provided with a clamping groove and the bottom provided with a cavity, fin-shaped heat dissipation structures are provided on two sides of the heat dissipation aluminum part and in the cavity, the cooling and heating sheet is clamped in the clamping groove, and the cooling fan is placed in the cavity of the heat dissipation aluminum part; the physiotherapy control circuit board 8 is mounted in the massage head cover 21, and the cooling fan is fixed in the massage head cover 21 and located above the physiotherapy control circuit board 8; and the massage head cover 21 is provided with a first heat dissipation hole corresponding to the cooling fan. Through the above structure, heat emitted by the cooling and heating sheet can be quickly dissipated to the outside of the massage gun through the heat dissipation aluminum part, the cooling fan, and the first heat dissipation hole. The temperature sensing element is an NTC thermistor.

The reciprocating driving mechanism 110 includes a motor, a crank 1101, and a connecting rod 1102, where the motor is arranged in the handle 11. An output shaft of the motor is connected to the crank 1101. One end of the connecting rod 1102 is coaxially connected to the crank 1101, and the other end thereof is in transmission connection with the aviation plug female connector 121 located in the housing 12. When the motor is running, the aviation plug female connector 121 and the aviation plug male connector 9 can be driven to reciprocate, so as to make the massage head 2 reciprocate in the axial direction.

Figure 6:
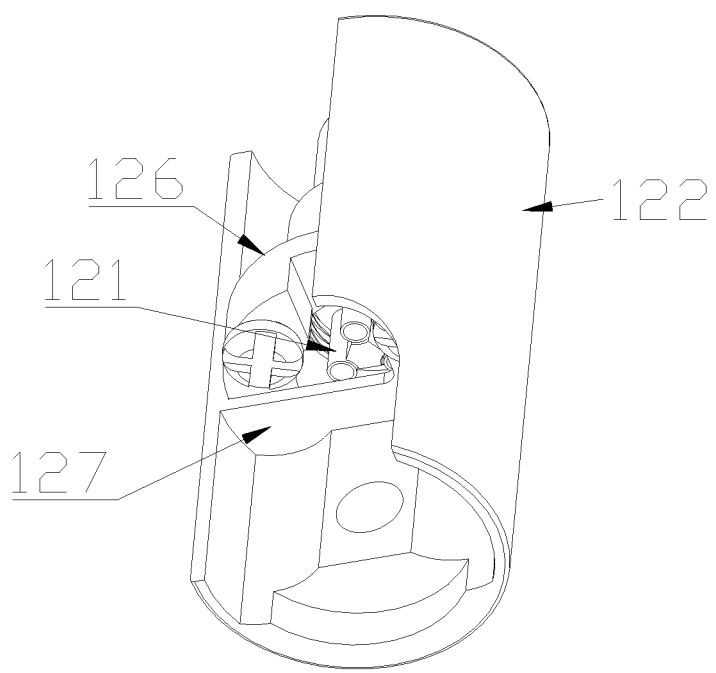
FIG. 6 is a second cross-sectional view of the massage gun according to the present disclosure when the piston part, the positioning part and the aviation plug female connector are assembled together.
Figure 7:
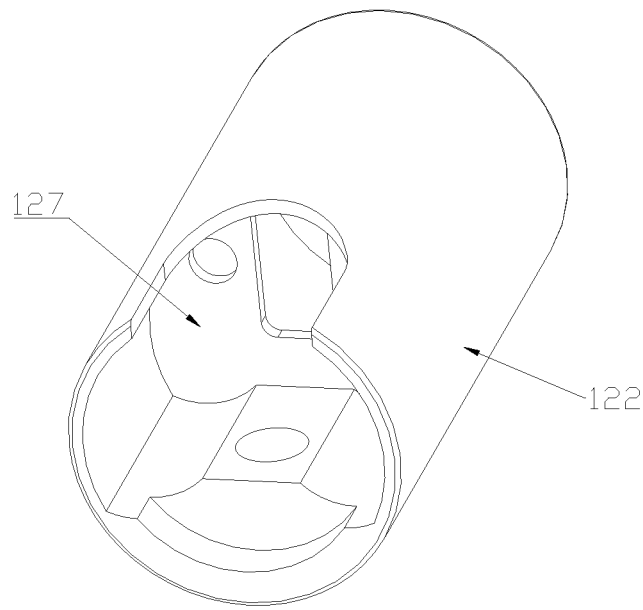
FIG. 7 is a schematic diagram of a stereostructure of the piston part in the massage gun according to the present disclosure.

As shown in FIG. 6 and FIG. 7, a piston part 122, a guide groove part 123, a guide groove silicon gel part 124, a seal cover 125, and a positioning part 126 are arranged in the housing 12, the guide groove part 123 is in contact connection with an inner wall of the housing 12 through the guide groove silicon gel part 124, the piston part 122 is slidably arranged in the guide groove part 123, the aviation plug female connector 121 passes through the seal cover 125 and is then screwed to the positioning part 126, the positioning part 126 is fixedly connected to a partition plate 127 in an inner cavity of the piston part 122, and the partition plate 127 is provided with a first opening for the connecting cable 4 to pass through; the positioning part 126 has a hollow structure with a cavity for accommodating the aviation plug female connector 121, and the connecting cable 4 passes through the first opening and then enters the inner cavity of the positioning part 126 to be riveted to the auxiliary connecting part 5.

In use, when the aviation plug male connector 9 is inserted into the aviation plug female connector 121, the massage head 2 can be in transmission connection with the reciprocating driving mechanism 110, and the cooling and heating assembly can further be electrically connected to power supply assembly 100.

Figure 3:
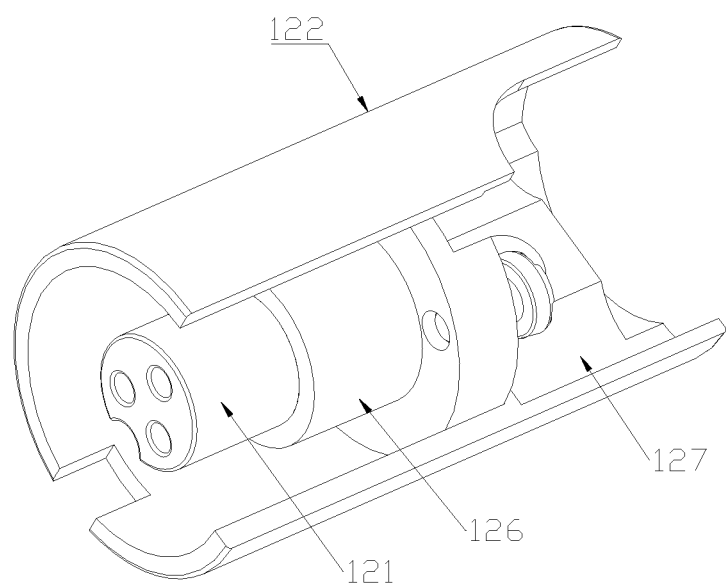
FIG. 3 is a first cross-sectional view of the massage gun according to the present disclosure when a piston part, a positioning part and an aviation plug female connector are assembled together.
Figure 8:
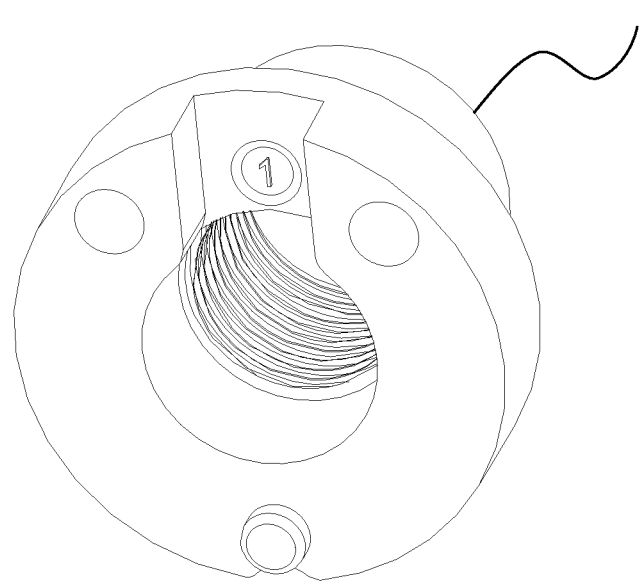
FIG. 8 is a schematic diagram of a stereostructure of the positioning piston part in the massage gun according to the present disclosure.

As shown in FIG. 3 and FIG. 8, specifically, the positioning part 126 is made of a plastic material and includes a clamping portion and a connecting portion, where the connecting portion has a hollow cylindrical structure with an inner wall provided with a threaded section; the clamping portion has a boss structure formed by extending outward and vertically from one end of the connecting portion, the specification and shape of the clamping portion are adapted to the specification and shape of the inner cavity of the piston part 122, the clamping portion is provided with a positioning hole, and a threaded hole is formed in a corresponding position of the partition plate 127.

It should be noted that the aviation plug has a plurality of holes for distinguishing between positive and negative poles and signal transmission; in order to ensure the correctness of the plug sequence, a plastic positioning part with a specific positioning function is adopted, and the aviation plug is fixed on the positioning part through threads, and then the positioning part is connected to a partition plate in an inner cavity of a piston part through two positioning holes, and is fixed at a rear end by using a screw.

It should be first noted here that "inward" refers to the direction toward the center of an accommodating space, and "outward" refers to the direction away from the center of the accommodating space.

In the description of the present disclosure, it should be understood that the orientation or positional relationship indicated by the terms "center", "longitudinal", "transverse", "length", "width", "thickness", "upper", "lower", "front", "rear", "left", "right", "vertical", "horizontal", "top", "bottom", "inner", "outer", "clockwise", "counterclockwise", "axial", "radial", and "circumferential" is based on the orientation or positional relationship shown in FIG. 1, and is only for the convenience of describing the present disclosure and simplifying the description, rather than indicating or implying that the apparatus or component referred to must have a specific orientation, be constructed and operated in a specific orientation, which therefore cannot be understood as a limitation to the present disclosure.

Moreover, the terms such as "first" and "second" are used only for the purpose of description and cannot be understood as indicating or implying relative importance or implicitly indicating the number of technical features indicated. Thus, features defined with "first" and "second" may explicitly or implicitly include at least one of the features. In the description of the present disclosure, "a plurality of" means at least two, such as two or three, unless otherwise specifically defined.

In the present disclosure, unless otherwise specified and defined, the terms such as "mount", "connected with", "connected to" and "fix" should be comprehended in a broad sense. For example, these terms may be comprehended as being fixedly connected, detachably connected or integrally connected; or mechanically connected, or electrically connected; or directly connected, or indirectly connected through an intermediate medium, or in an internal communication between two elements or an interactive relationship between two elements, unless otherwise clearly defined. A person of ordinary skill in the art may understand specific meanings of the foregoing terms in the present disclosure based on a specific situation.

In the present disclosure, unless otherwise specified and limited, a first component being "on" or "beneath" a second component means that the first component is in direct contact with the second component, or the first component is in indirect contact with the second component through an intermediate medium. Furthermore, if the first component is "above" the second component, it means that the first component is over or obliquely above the second component, or only means that the level of the first component is greater than that of the second component. If the first component is "below" the second component, it means that the first component is under or obliquely below the second component, or only means that the level of the first component is less than that of the second component.

In the description of this specification, descriptions referring to the terms "one embodiment", "some embodiments", "example", "specific example", or "some examples" mean that specific features, structures, materials or characteristics described with reference to this embodiment or example are included in at least one embodiment or example of the present disclosure. In the specification, the illustrative expressions of the above terms do not necessarily refer to the same embodiments or examples. Furthermore, the specific features, structures, materials or characteristics described may be combined in any one or more embodiments or examples in a suitable manner. In addition, those skilled in the art can combine the different embodiments or examples and the features of the different embodiments or examples described in the specification without contradicting with each other.

The above descriptions are only specific implementations of the present disclosure, but the protection scope of the present disclosure is not limited thereto. Any person skilled in art can easily conceive of variations or replacements within the technical scope disclosed in the present disclosure, and the variations or replacements should fall within the protection scope of the present disclosure. Therefore, the protection scope of the present disclosure should be subject to the claims.

What is claimed is:

1. A massage gun, comprising a gun body, a massage head arranged on the gun body, an auxiliary physiotherapy assembly arranged in the massage head, a main circuit board arranged in the gun body, and a connecting cable electrically connected to the auxiliary physiotherapy assembly and the main circuit board, wherein the connecting cable is made of a conductive wire resistant to high-speed bending;

wherein an auxiliary connecting part is further arranged between the connecting cable and the auxiliary physiotherapy assembly, and the auxiliary connecting part is made of a weldable conductive material;

wherein the gun body comprises a handle and a housing connected perpendicular to the handle, and a wire bridge structure for the connecting cable to pass through is provided on an opening structure of the handle corresponding to the housing;

wherein the auxiliary physiotherapy assembly comprises a physiotherapy module, a physiotherapy control circuit board, and an aviation plug male connector that are electrically connected in sequence, an aviation plug female connector detachably and electrically connected to the aviation plug male connector is arranged in the housing, and the auxiliary connecting part is welded to the aviation plug female connector.

2. The massage gun according to claim 1, wherein one end of the auxiliary connecting part is riveted to the connecting cable, and the other end thereof is welded to the auxiliary physiotherapy assembly.

3. The massage gun according to claim 1, wherein the auxiliary connecting part is made of a copper material.

4. The massage gun according to claim 1, wherein a piston part, a guide groove part, a guide groove silicon gel part, a seal cover, and a positioning part are arranged in the housing, the guide groove part is in contact connection with an inner wall of the housing through the guide groove silicon gel part, the piston part is slidably arranged in the guide groove part, the aviation plug female connector passes through the seal cover and is then screwed to the positioning part, the positioning part is fixedly connected to a partition plate in an inner cavity of the piston part, and the partition plate is provided with a first opening for the connecting cable to pass through; the positioning part has a hollow structure with a cavity for accommodating the aviation plug female connector, and the connecting cable passes through the first opening and then enters the inner cavity of the positioning part to be riveted to the auxiliary connecting part.

5. The massage gun according to claim 4, wherein the positioning part is made of a plastic material and comprises a clamping portion and a connecting portion, and the connecting portion has a hollow cylindrical structure with an inner wall provided with a threaded section; the clamping portion has a boss structure formed by extending outward and vertically from one end of the connecting portion, the specification and shape of the clamping portion are adapted to the specification and shape of the inner cavity of the piston part, the clamping portion is provided with a positioning hole, and a threaded hole is formed in a corresponding position of the partition plate.

\* \* \* \* \*